(12) United States Patent
Hirano et al.

(10) Patent No.: US 6,495,822 B2
(45) Date of Patent: Dec. 17, 2002

(54) ATOMIC BEAM GENERATING METHOD AND DEVICE

(75) Inventors: Takuya Hirano, Tokyo (JP); Yoshio Torii, Tokyo (JP); Kenichi Ito, Tokyo (JP); Ryo Namiki, Kanagawa (JP)

(73) Assignee: Japan Science and Technology Corporation, Kawaguchi (JP)

( * ) Notice: Subject to any disclaimer, the term of this patent is extended or adjusted under 35 U.S.C. 154(b) by 0 days.

(21) Appl. No.: 09/926,699

(22) PCT Filed: Mar. 8, 2001

(86) PCT No.: PCT/JP01/01820

§ 371 (c)(1),
(2), (4) Date: Dec. 4, 2001

(87) PCT Pub. No.: WO01/95677

PCT Pub. Date: Dec. 13, 2001

(65) Prior Publication Data

US 2002/0134931 A1 Sep. 26, 2002

(30) Foreign Application Priority Data

Jun. 2, 2000 (JP) ........................................ 2000-166768

(51) Int. Cl.[7] .................................................. H05H 3/02
(52) U.S. Cl. ...................................... 250/251; 250/251
(58) Field of Search ......................................... 250/251

(56) References Cited

FOREIGN PATENT DOCUMENTS

| JP | 2-68835 | 3/1990 |
|---|---|---|
| JP | 2-288048 | 11/1990 |
| JP | 3-101419 | 4/1991 |
| JP | 6-112551 | 4/1994 |
| JP | 6-119998 | 4/1994 |
| JP | 7-316790 | 12/1995 |

OTHER PUBLICATIONS

Y. Torii, et al; Slow Atomic Beam from a Magneto–Optical Trap, Department of Physics, Gakushuin University.
K. Ito, et al; Characteristics of Double MOT for Bose–Einstein Condensation, Department of Physics, Gakushuin University.

Primary Examiner—Bruce Anderson
Assistant Examiner—Zia R. Hashmi
(74) Attorney, Agent, or Firm—Armstrong, Westerman & Hattori, LLP

(57) ABSTRACT

A atomic beam generating method and apparatus for producing an atomic beam that is high in flow rate is disclosed which makes vacuum equipment simpler in construction, and is high in the rate of extraction of atoms, capable of adjusting its flow rate and applicable to many different atomic species. The atomic beam generating apparatus used produces a beam of atoms by extracting the atoms from a low temperature atomic cloud formed by laser cooling. The low temperature atomic cloud is formed by irradiating the atoms with at least two sets of laser lights in a region of laser beam intersection in which they intersect, each of the sets of laser lights being made of a pair of laser beams which are opposite in direction of travel to each other, the laser beams intersecting in the region of laser beam intersection. In this region of laser beam intersection there is provided a laser beam shading zone in which one of the laser beams in each of the sets of laser lights that is traveling in a particular direction is obstructed to provide a shade therefor. The laser beam shading zone is so located in the region of laser beam intersection that in the laser beam shading zone a force is brought about that is effective to force atoms in the laser beam shading zone to move towards a preselected direction, thereby forming a beam thereof.

10 Claims, 10 Drawing Sheets

US 6,495,822 B2

ATOMIC BEAM GENERATING METHOD AND DEVICE

TECHNICAL FIELD

This invention relates to an atomic beam generating method and apparatus for producing a low velocity beam of atoms.

BACKGROUND ART

The conventional methods of producing an atomic beam are classified into the method whereby atoms placed under an elevated pressure or at a raised temperature are injected into a vacuum and the method that utilizes magneto-optical trapping as one of laser cooling techniques.

The method of injecting into vacuum requires atoms if in a solid state at a room temperature to be heated to a high temperature in an oven. An atomic beam that can be obtained by the injection method has an average velocity as high as about several hundred meters/second and a velocity distribution that largely spreads out.

In contrast, the method in which magneto-optical trapping is utilized makes it possible to produce a low velocity atomic beam that is as slow as several centimeters/second.

Magneto-optical trapping is a technique that associates a Doppler cooling process using a laser light with a central force produced according to a Zeeman shift of an atomic level by a quadruple magnetic field, which forms a low temperature atomic cloud having a temperature as low as about 1 micro-degree Kelvin. See Phys. Rev. Lett. 59, 2631 (1987), E. L. Raab et al and Applied Physics (in Japan), 60, 864 (1991), SHIMIZU, Fujio. The Doppler cooling process referred to above is a process in which atoms are irradiated with laser lights of a frequency slightly lower than the resonant frequency of the atoms, which are directed towards the atoms from six or four different directions. In this process, increases by Doppler shifts in the probabilities of absorption of the atoms moving towards the laser lights are exploited to effect three dimensional cooling thereof. See Phy. Rev. Lett. 55, 48 (1985), S. Chu et al.

As the atoms magneto-optically trapped are cooled to a temperature of 100 micro-degrees Kelvin or so, extracting the atoms trapped effectively enables a beam of atoms moving at a low velocity to be produced. In such a background, there have already been realized two methods of extraction of trapped atoms, viz. first by using a mirror with a hole designed to provide a shade for one of the cooling laser beam (see Phy. Rev. Lett. 77, 3331 (1996), Z. T. Lu et al) and second by changing the internal state of the trapped atoms (Nature, 380, 691 (1996), J. Fujita et al).

FIG. 10 is a diagrammatic view for the illustration of the conventional method in which a perforated mirror (a mirror with a hole) is used to obstruct one of cooling laser beams and to hinder it from reflecting.

In FIG. 10, there are shown vacuum chambers 70 and 71, low temperature atomic cloud 73 and 74 magneto-optically trapped and thereby held in place, laser beams 7a, 7b, 7c, 7d and 7e for three dimensionally trapping the atoms and forming such two low temperature clouds of these atoms and so holding them by Doppler-cooling the atoms. A mirror 72 is associated with one of the laser beams 7b for reflecting the laser beam 7b and is formed in its center with a hole 75. The hole 75 is designed to provide a shade for the laser beam 7b for irradiating the low temperature atomic cloud 73 therewith. The atoms located in the low temperature atomic cloud 73 thus so shaded from irradiation with the laser beam 7b gain a force directed downwards as shown in FIG. 10 and as a result a beam of the atoms is produced. The atomic beam so produced passes through the hole 75 and a transport tube 77 and is transported to the low temperature atomic cloud 74.

FIG. 10 is a diagrammatic view for the illustration of the conventional method in which a perforated mirror (a mirror with a hole) is used to obstruct one of cooling laser beams and to hinder it from reflecting.

In the method using such a hole formed mirror to provide a shade for one of cooling laser beams, however, extracting an atomic beam in an exploitable state requires the mirror to be incorporated into vacuum equipment. See Phys. Rev. A58, 3891 (1998). This poses problems such as those of the vacuum equipment becoming complicated and the mirror that may be contaminated. Furthermore, the atomic beam spreading in its velocity direction causes a portion thereof to become intercepted by the mirror, which prevents the produced atomic beam from its effective extraction.

The other method, in which the internal state of atoms is varied, irradiates the atoms with a laser light that is different in wavelength from their trapping laser light to shift the atoms to an energy level at which they do not absorb the trapping laser light, thereby releasing them from their trapped state. This renders the method applicable only to those atomic species that possess a proper energy level at which the atoms do not absorb their trapping laser light. Also, a portion of atoms that absorbed the laser light for freeing them from trapping may have shifted to an unusable energy level, which reduces the efficiency of usable extraction. See Phy. Rev. A46, R17 (1992).

It should also be noted that while atomic beams can be useful in various technical fields including high resolution spectroscopy, frequency standard, atomic wave interferometers, Bose condensation atom formation, atomic ray lithography and atomic ray surface analysis, their application to these utilizations makes it essential that they be controllable in flow rate. It has so far been difficult to control the flow rate of an atomic beam, however.

With the foregoing points taken into account, the present invention is aimed to provide an atomic beam generating method and apparatus that can produce an atomic beam with simpler vacuum equipment and at an enhanced efficiency of extraction while making its flow rate controllable and that can produce beams of atoms in an expanded range of atomic species.

DISCLOSURE OF THE INVENTION

In order to achieve the object mentioned above, the present invention as set forth in claim 1 in the claims appended hereto, provides an atomic beam generating method for producing an atomic beam by extracting atoms from a low temperature atomic cloud formed utilizing laser cooling, which method comprises the steps of forming a low temperature atomic cloud by irradiating the atoms with at least two sets of laser lights in a region of laser beam intersection in which they intersect, each of the sets of laser lights being made of a pair of laser beams which are opposite in direction of travel to each other, the laser beams intersecting in the said region of laser beam intersection; and providing in the said region of laser beam intersection a laser beam shading zone in which a portion of one of the laser beams in each of the sets of laser lights that is traveling in a particular direction is obstructed to provide a shade therefor, wherein the said laser beam shading zone is so located in the said region of laser beam intersection that in the said laser beam shading zone a force is brought about that is effective to force atoms in the said laser beam shading zone to move towards a predetermined direction, thereby forming a beam thereof.

In an atomic beam generating method, the present invention as set forth in claim 2 in the appended claims provides that the said laser beam shading zone is created by a tube for transporting the said beam of atoms, the said tube obstructing the said one of the laser beams in each of the sets to provide the said shade therefor.

A method as described above enables a force of high strength to push atoms to be provided and hence the atoms to be extracted efficiently, thereby producing an atomic beam effectively. Also, disusing the internal state of atoms makes the method applicable to atoms of practically all of the atomic species. Further, the method no longer requires a mirror to be incorporated in vacuum equipment and hence makes the vacuum equipment simple in construction and the mirror free from contamination.

In an atomic beam generating method, the present invention as set forth in claim 3 in the appended claims further provides adjusting the flow rate of the said beam of atoms that the said atomic beam transporting tube transports, by applying a magnetic field to the said low temperature atomic cloud to change its position in the said region of laser beam intersection so as to change the distance between the said low temperature atomic cloud and an upper end of the said atomic beam transporting tube.

Alternatively in an atomic beam generating method, the present invention as set forth in claim 4 in the appended claims further provides adjusting the flow rate of the said beam of atoms by irradiating the said low temperature atomic cloud with an additional laser beam to force atoms in the said low temperature atomic cloud aside into the said laser beam shading zone.

In an atomic beam generating method, the present invention also provides that the said additional laser beam has a wavelength with which it resonates with atoms in the said low temperature atomic cloud.

These methods make it possible to adjust the flow rate of an atomic beam being produced.

The present invention as set forth in claim 6 in the appended claims also provides an atomic beam generating apparatus for producing an atomic beam by extracting atoms from a low temperature atomic cloud formed utilizing laser cooling, which apparatus comprises: a laser system for forming a low temperature atomic cloud by irradiating the atoms with at least two sets of laser lights in a region of laser beam intersection in which they intersect, each of the sets of laser lights being made of a pair of laser beams which are opposite in direction of travel to each other, the laser beams intersecting in the said region of laser beam intersection; and a means for providing in the said region of laser beam intersection a laser beam shading zone in which a portion of one of the laser beams in each of the sets of laser lights that is traveling in a particular direction is obstructed to provide a shade therefor, wherein the said means is adapted to so locate the said laser beam shading zone in the said region of laser beam intersection that in the said laser beam shading zone a force is brought about that is effective to force atoms in the said laser beam shading zone to move towards a predetermined direction, thereby forming a beam thereof.

In an atomic beam generating apparatus, the present invention as set forth in claim 7 in the appended claims also provides that the said means for providing the laser beam shading zone comprises a tube for transporting the said beam of atoms, the said tube being arranged to obstruct the said one of the laser beams in each of the sets to provide the said shade therefor.

An apparatus as described above enables a force of high strength to push atoms to be provided and hence the atoms to be extracted efficiently, thereby producing an atomic beam effectively. Also, disusing the internal state of atoms makes the apparatus applicable to atoms of practically all of the atomic species. Further, the apparatus no longer requires a mirror to be incorporated in vacuum equipment and hence makes the vacuum simpler in construction and the mirror free from contamination.

In an atomic beam generating apparatus, the present invention as set forth in claim 8 in the appended claims further provides means for applying a magnetic field to the said low temperature atomic cloud to change its position in the said region of laser beam intersection so as to change the distance between the said low temperature atomic cloud and an upper end of the said atomic beam transporting tube, thereby adjusting the flow rate of the said beam of atoms that the said atomic beam transporting tube transports.

In an atomic beam generating apparatus, the present invention as set forth in claim 9 in the appended claims further provides that the said laser system is adapted to irradiate the said low temperature atomic cloud with an additional laser beam to force atoms in the said low temperature atomic cloud aside into the said laser beam shading zone, thereby adjusting the flow rate of the said atomic beam.

In an atomic beam generating apparatus, the present invention as set forth in claim 10 in the appended claims further provides that the said additional laser beam has a wavelength with which it resonates with atoms in the said low temperature atomic cloud.

BRIEF DESCRIPTION OF THE DRAWINGS

The present invention will better be understood from the following detailed description and the drawings attached hereto showing certain illustrative forms of embodiment of the present invention. In this connection, it should be noted that such forms of embodiment illustrated in the accompanying drawings hereof are intended in no way to limit the present invention but to facilitate an explanation and understanding thereof.

In the drawings.

BEST MODES FOR CARRYING OUT THE INVENTION

Figure 1:
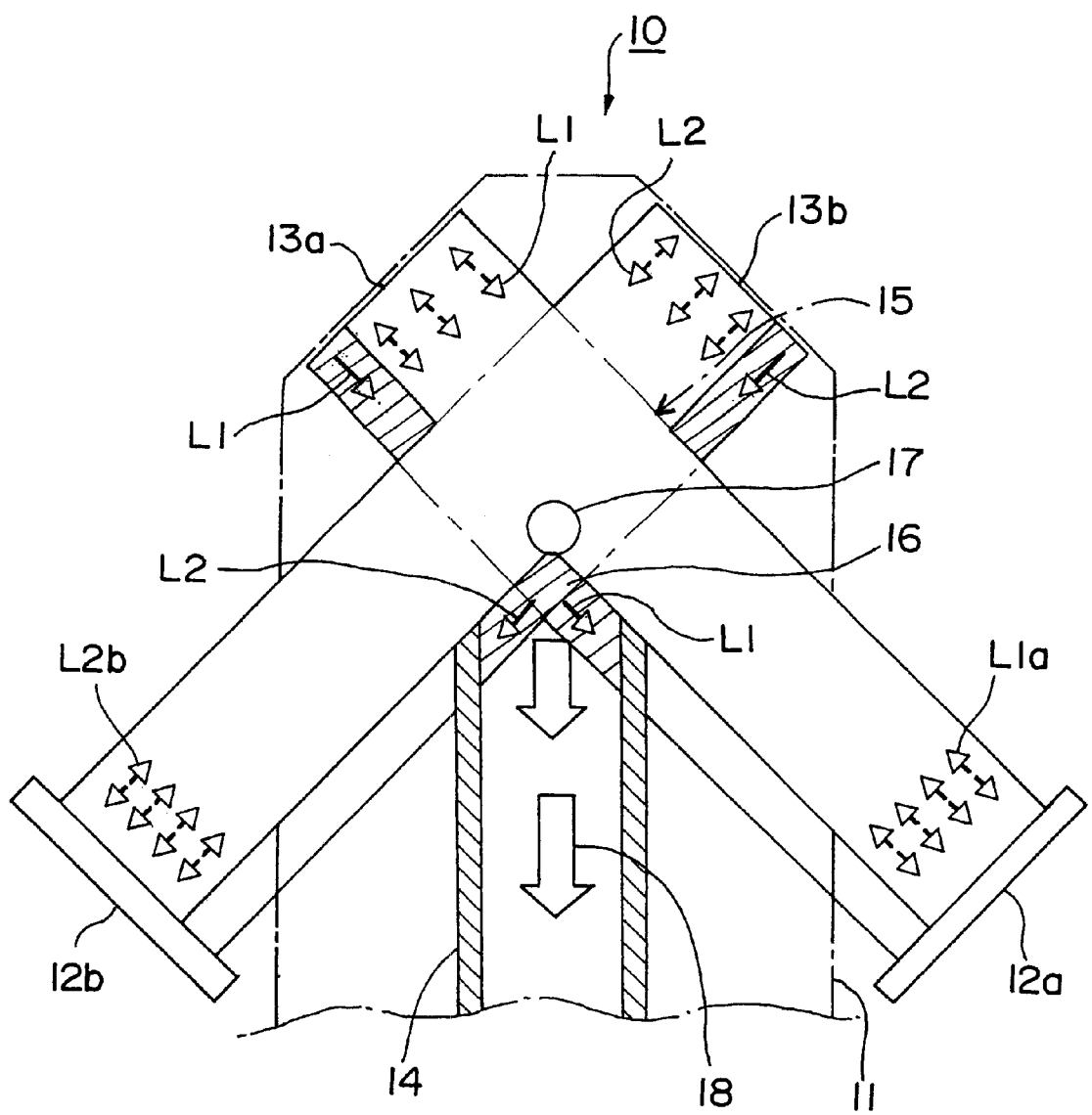
FIG. 1 is a diagrammatic view illustrating an atomic beam generating method that represents a certain form of embodiment of the present invention.

Hereinafter, an atomic beam generating method and apparatus according to the present invention will be described in detail with respect to presently best forms of embodiments thereof illustrated in the drawing figures.

FIG. 1 is a diagrammatic view for the illustration of an atomic beam generating apparatus that represents such a form of embodiment of the present invention.

As shown in FIG. 1, an atomic beam generating apparatus 10 includes a vacuum chamber 11, a laser system comprising a pair of laser sources (not shown) which are disposed outside of the vacuum chamber 11 and a pair of mirrors 12a and 12b which are also disposed outside of the vacuum chamber 11 to form a pair of laser lights 13a and 13b, and a transport tube 14 through which low temperature atoms are to be extracted in the form of a beam.

The vacuum chamber 11 is provided, though not shown in FIG. 1, with an ampoule 25 (shown in FIG. 2), and has a third laser light directed perpendicular to the face of the drawing and oriented to intersect a region in which the laser lights 13a and 13b intersect.

The laser light 13a as shown in FIG. 1 is made of a laser beam L1 traveling from the upper left towards the lower right, and a laser beam L1a formed from the laser beam L1 past the vacuum chamber 11 upon its reflection by the mirror 12a disposed and oriented perpendicular thereto, the laser beam L1a then traveling in the opposite direction to that in which the laser beam L1 travels.

On the other hand, the laser light 13b as shown in FIG. 1 is made of a laser beam L2 traveling from the upper right towards the lower left, and a laser beam L2b formed from the laser beam L2 past the vacuum chamber 11 upon its reflection by the mirror 12b disposed and oriented perpendicular thereto, the laser beam L2b then traveling in the opposite direction to that in which the laser beam L2 travels.

Further, the third laser light not shown is made of a laser beam, and a laser beam that is formed from this laser beam past the vacuum chamber 11 upon its reflection by a third mirror disposed and oriented thereto, the latter laser beam then traveling in the opposite direction to that in which the former laser beam travels.

In this way, three sets of laser lights each made of a pair of laser beams traveling in mutually opposite directions are formed so as to intersect in the region of intersection 15.

The transport tube 14 is a tube provided to extract a low velocity atomic beam therethrough. The transport tube 14 as shown in FIG. 1 has its upper end so located as to obstruct a portion of each of the laser beams L1 and L2. Laser beam shading zones are thereby formed in which absent those laser beam parts L1a and L2b obstructed and shaded by the upper end of the transport tube 14, only the laser beam L1 part does, only the laser beam L2 part does and both the laser beams L1 and L2 parts do exist, respectively.

Although not shown in FIG. 1, the atomic beam generating apparatus 10 is also provided with coils for forming a magnetic trap such as to envelope the laser beam intersecting zone 15. These coils (shown in FIG. 3 and indicated by reference character 31) are designed to establish a quadruple magnetic field in which the field strength is zero at its center and increases as this center is departed from. Also provided is a wave-plate (not shown) disposed outside of the vacuum chamber 11 for properly controlling polarization of the laser beams.

Next, a form of embodiment of how an atomic beam is generated in accordance with the present invention is explained by reference to the atomic beam generating apparatus 10.

First, the vacuum chamber 11 is furnished with atoms from an atom supply ampoule and then brought to and held at a preestablished vacuum. Thereafter, the laser beams including L1 and L2 are injected and the magnetic trap is brought into operation.

This causes the laser beams L1 and L2 and the third laser beam and the laser beams L1a and L2b formed on reflection by the mirrors 12a and 12b and the third reflection formed laser beam, which are six in total number, to irradiate the region of their intersection 15 therewith from ±x, ±y and ±z directions. The atoms that exist in the intersection region 15, if moved out in any of these directions, will upon colliding with the incoming laser beam be forced back and thereby entrapped. Doppler cooling also acts on these atoms and there results a cloud of low temperature atoms 17. Applying the magnetic field to the atoms enhances their entrapping effect and facilitates forming such a cloud 17 of low temperature atoms 17. Thus, a method of trapping or entrapping atoms both optically and magnetically is called magneto-optical trapping or entrapping.

Stated otherwise here, the atoms that exist in the region of intersection 15 are magneto-optically trapped or entrapped and also subjected to Doppler cooling, forming a low temperature atomic cloud 17.

Of the atoms in the low temperature atomic cloud 17, those which come to lie in the laser beam shading zones 6 in which only the laser beam L1 exists, only the laser beam L2 exists and both the laser beams L1 and L2 exist, respectively, are forced out in particular directions determined by the directions in which the laser beam L1 travels, the laser beam L2 travels and the laser beams L1 and L2 travel in these respective regions 16. They eventually are forced out, as shown in FIG. 1, downwards into and through the transport tube 14. Hence, there is produced a beam of atoms 18 as indicated by the arrows in FIG. 1.

The laser beam shading zone 16 is provided directly above the transport tube 14 and is also arranged so that a portion of the zone 16 enters into the transport tube 14. This permits the atoms forced out though having a spread in their velocity direction to be almost all taken into the transport tube 14. Consequently, the atoms are effectively extracted and a low velocity atomic beam 18 is produced efficiently.

Therefore, the atomic beam generating method according to the present invention makes it possible to produce in this way an atomic beam efficiently.

It will also be seen that the mirrors 12a and 12b and the third mirror each located outside of the vacuum chamber 11 are freed from contamination and also make the vacuum equipment simpler in construction.

To be noted further is the advantage that disusing the internal state of atoms in producing a beam thereof gives the method and apparatus the ability to extract atoms without regard to their atomic species.

Mention is next made of a specific example of the atomic beam generating method described above.

Figure 2:
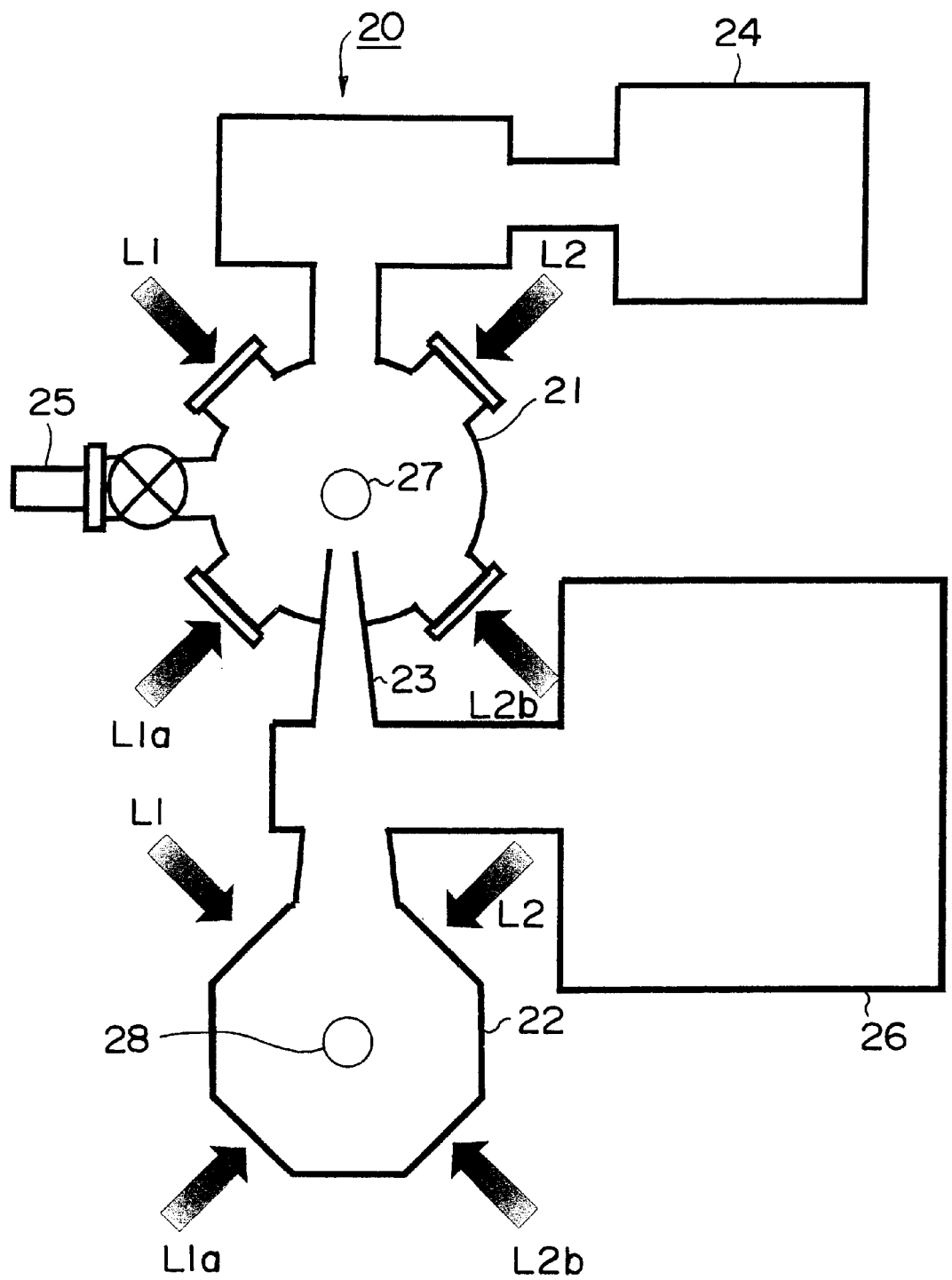
FIG. 2 is a diagrammatic view illustrating the construction of a double magneto-optical trapping apparatus in which a Bose-Einstein condensation of a gas of Rb (rubidium) atoms is realized utilizing an atomic beam generating apparatus according to the present invention.

FIG. 2 is a diagrammatic view illustrating the construction of a double magneto-optical trapping apparatus in which a Bose-Einstein condensation of a gas of Rb (rubidium) atoms (cf. Science, 269, 198 (1995) M. H. Anderson et al.; Laser Research (in the Japanese), 28, 147 (2000) TORII, Toshio) is realized utilizing an atomic beam generating arrangement 10 as shown in FIG. 1.

As shown in FIG. 2, the double magneto-optical trapping apparatus 20 includes a pair of vacuum chambers 21 and 22 and a transport tube 23 that connects to them.

The vacuum chamber 21 shown in the upper side has a magneto-optical trap constructed in the same way as in the atomic beam generating apparatus 10 of the present invention shown in FIG. 1, and is provided with an ion pump 24 with a rate of evacuation of 20 liters per second and a Rb (rubidium) ampoule 25.

The transport tube 23 is functionally the same as the transport tube 14 shown in and described in connection with FIG. 1, and in this example is tapered having an upper end diameter of 4 mm, a lower end diameter of 12 mm and a length of 62 mm.

The vacuum chamber 22 in the lower side is connected via the transport tube 23 to the upper vacuum tube 21, and is provided with a Ti sublimation pump 26 with a rate of evacuation of 150 liters per second to enable the vacuum chamber 22 to be maintained at a vacuum of $10^{-11}$ Torr. The vacuum chamber 22 is also provided with a magneto-optical trap as in the vacuum chamber 21.

According to the double magneto-optical trapping apparatus 20, supplying the upper chamber 21 with Rb atoms from the Rb ampoule 25 to form therein a background gaseous atmosphere made up of Rb atoms at a vacuum $10^{-8}$ Torr permits a low temperature atomic cloud 27 made of Rb atoms of $10^8$ in number to be quickly produced in the magneto-optical trap in the upper vacuum chamber 21 in no more than 1 second. Rb atoms in this low temperature cloud 27 subjected to the atomic beam generating method of the present invention are forced efficiently into the transport tube 23 and in the form of a beam of the atoms is transported into the magneto-optical trap in the lower vacuum 22, becoming a low temperature atomic cloud 28 therein.

The lower chamber is held at a vacuum as high as $10^{-11}$ Torr, which enables the low temperature cloud of Rb atoms 28 formed in the magneto-optical trap in the lower vacuum chamber 22 to be longer in life, being capably extant for a time period as long as about 10 minutes.

It has thus been demonstrated that a Bose-Einstein condensation of Rb atoms lasting for an extended time period can be produced utilizing the atomic beam generating apparatus according to the present invention.

Mention is next made of another form of embodiment of the atomic beam generating method according to the present invention.

Figure 3:
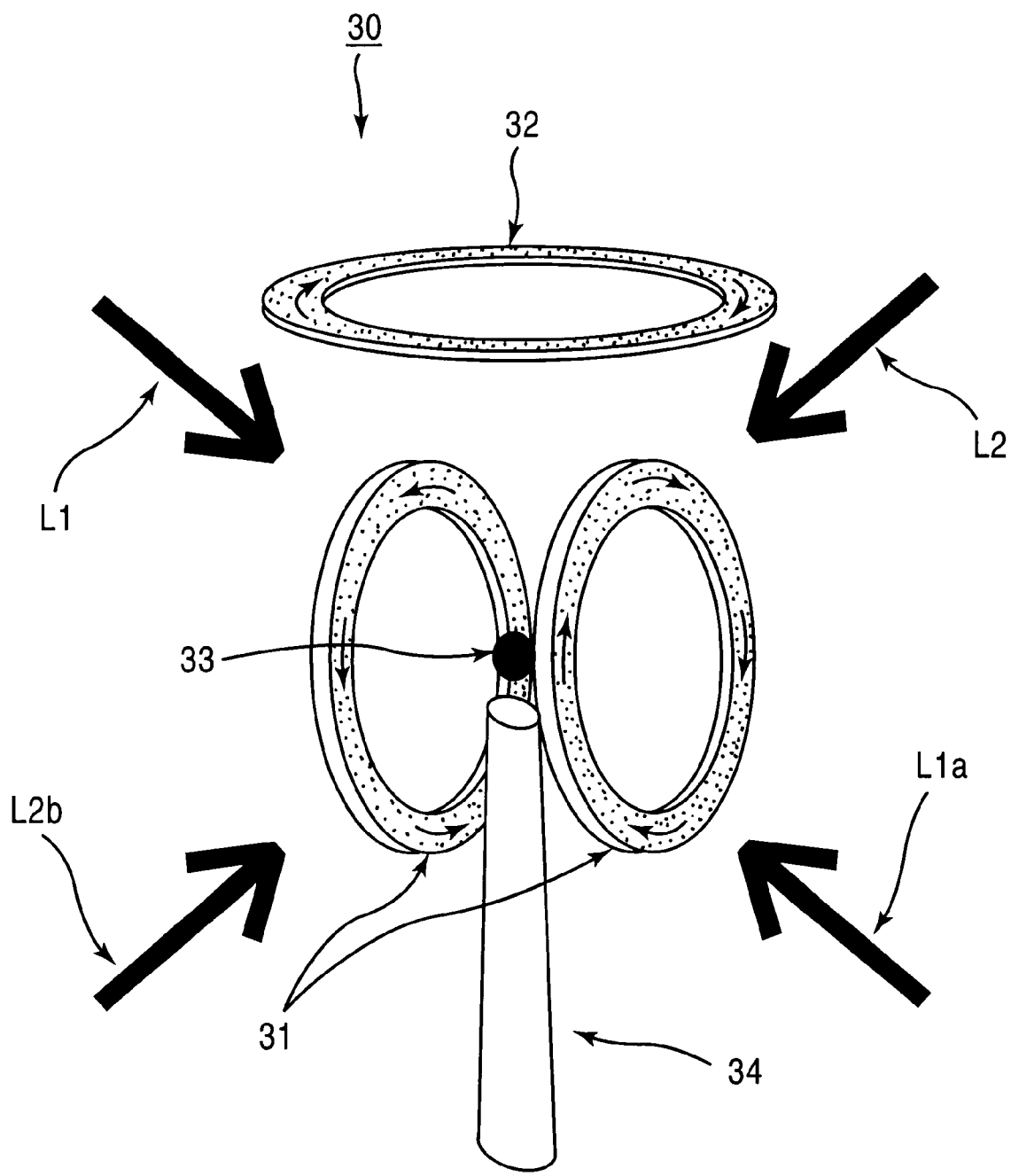
FIG. 3 is a diagrammatic view for the illustration of an atomic beam generating apparatus that represents another form of embodiment of the present invention.

FIG. 3 is a diagrammatic view for the illustration of an atomic beam generating apparatus that represents another form of embodiment of the present invention.

As shown in FIG. 3, an atomic beam generating apparatus 30 is constructed by incorporating a position adjustment coil 32 into the atomic beam generating apparatus 10 shown in and described in connection with FIG. 1.

While the magnetic field formed by the quadruple magnetic field generating coils 31 is a quadruple magnetic field that has its field strength of zero at a point in the laser beam intersecting region 15 shown in FIG. 1 and increasing as this point is departed from, superimposing a magnetic filed upon the quadruple magnetic field by passing an electric current through the position adjustment coil 32 permits the position of the point at which the field strength is zero to vary. Since the low temperature atomic cloud 33 is magnetically entrapped about the point at which the field strength is zero, adjusting the current passed through the position adjustment coil 32 to adjust the position of the point at which the field strength is zero permits the distance between the low temperature atomic cloud 33 and the upper end of the transport tube 34 to be adjusted.

Making the low temperature atomic cloud 33 closer to the upper end of the transport tube 34 causes a part larger of the low temperature atomic cloud 33 to enter into the laser beam shading zone 16 shown in FIG. 1, and thus more in number of the low temperature atoms to be forced out into the transport tube 34 and consequently permits an atomic beam of atoms larger in number to be produced. Thus, the atomic beam generating method set forth in claim 3 in the claims provides adjusting the flow or flow rate of an atomic beam by adjusting the magnitude of current passed through the position adjustment coil means 32.

While the position adjustment coil means is shown in FIG. 3 as made of the single coil 32, it should be noted that the position adjustment coil means is not so limited but may comprise a pair of coils so disposed as to encircle the region 15 where the laser beams L1 and L2 intersect as shown in FIG. 1.

Mention is next made of a specific implementation of the atomic beam generating method shown in FIG. 3.

FIG. 4 shows exemplary picture images, taken by a CCD camera, of an atomic beam having its flow rate adjustably varied using the atomic beam generating apparatus shown in FIG. 3.

Figure 4A:
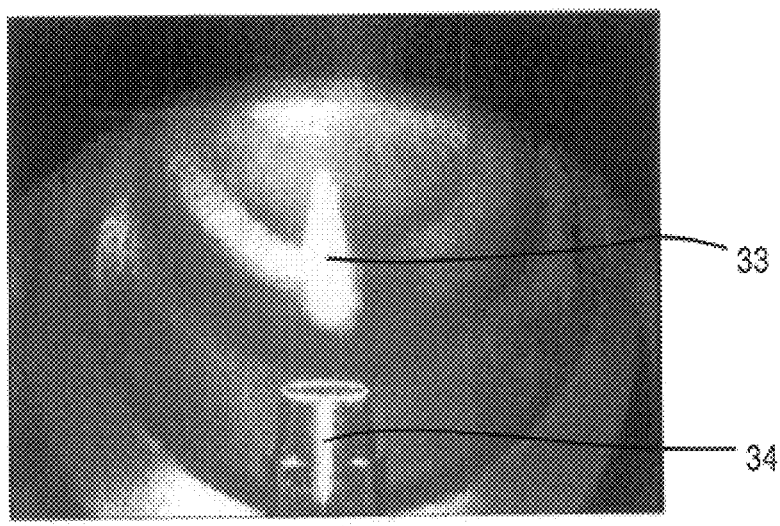
FIG. 4 shows typical picture images, taken by a CCD camera, of varied states of an atomic beam having its flow rate adjustably varied using the atomic beam generating apparatus shown in FIG. 2.

FIG. 4(A) shows a picture image when the position adjustment coil 32 has no current passed therethrough. What is seen like an eggplant and white is a cloud of low temperature Rb atoms 33.

Figure 4B:
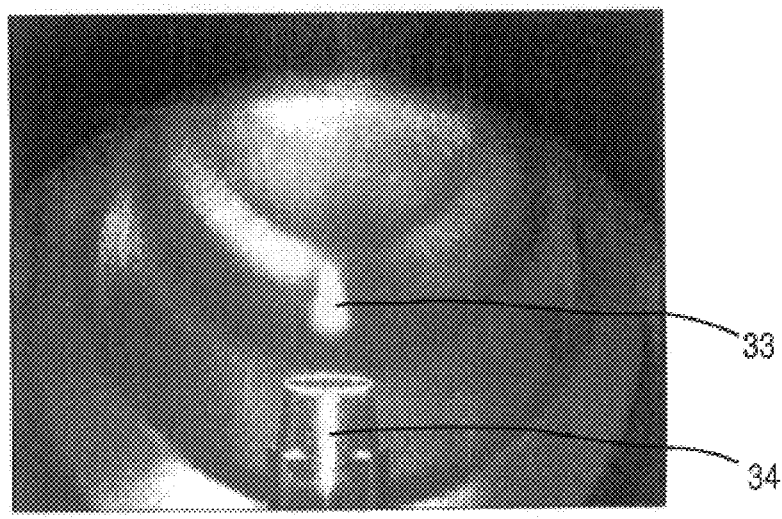
Figure 4C:
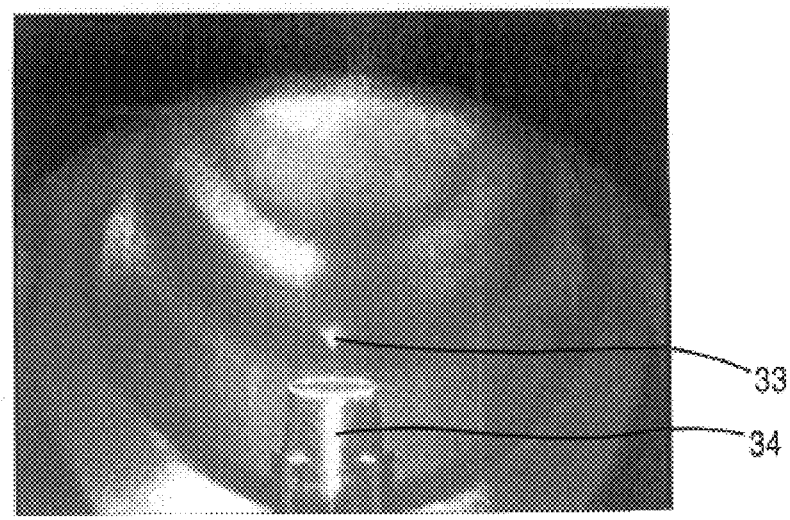

The point at which the magnetic field strength is zero is located above the low temperature atomic cloud 33. This is due to the fact that the upwardly traveling laser beams L1a and L2b having losses by the mirrors 12a and 12b is lower in strength than the downwardly traveling laser beams L1 and L2. The tube seen below it is the transport tube 34. FIG. 4(B) shows a picture image taken when the position adjustment coil 32 has an electric current passed therethrough. It is seen that the zero point for the magnetic field is shifted downwards and at the same time the low temperature atomic cloud 33 is made smaller by entering into the laser beam shading region 16, thereby permitting a larger number of atoms to be led into the transport tube 34. From FIG. 4(C) that shows a picture image taken when the position adjustment coil 32 has an increased magnitude of current passed through it, it is seen that the low temperature atomic cloud 33 is further reduced in size.

Figure 5:
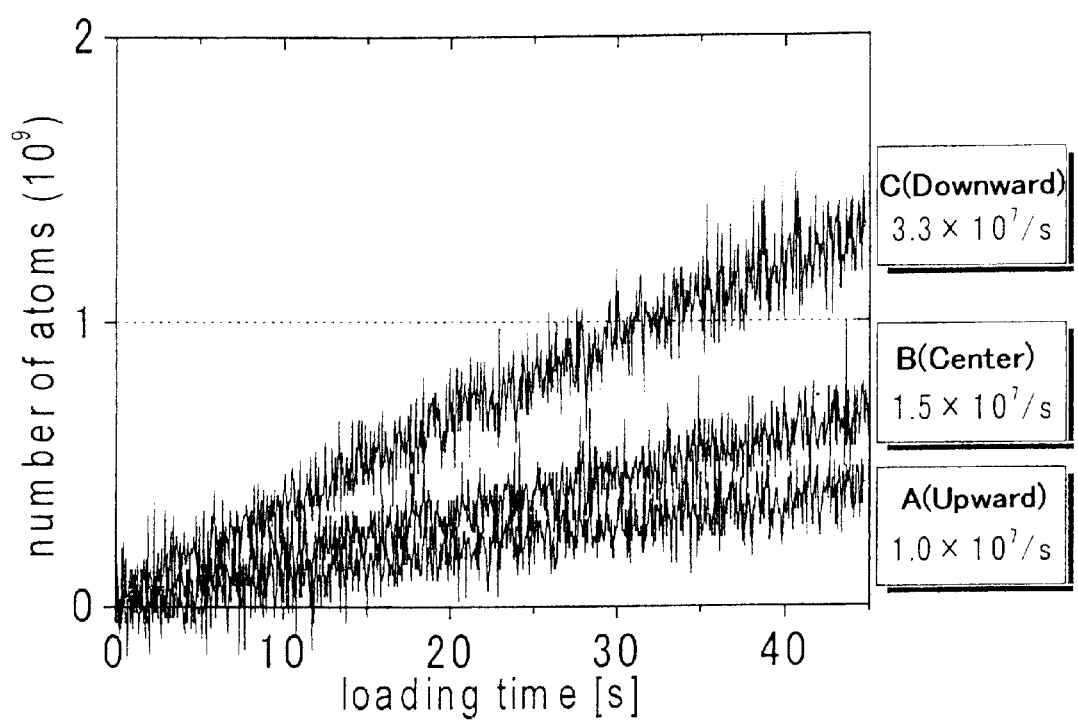
FIG. 5 shows typical results of measurement in which the flow rate is measured in the varied states shown in FIG. 4.

FIG. 5 shows results of measurement in which the flow rate is measured in the varied states indicated in FIG. 4.

Figure 6:
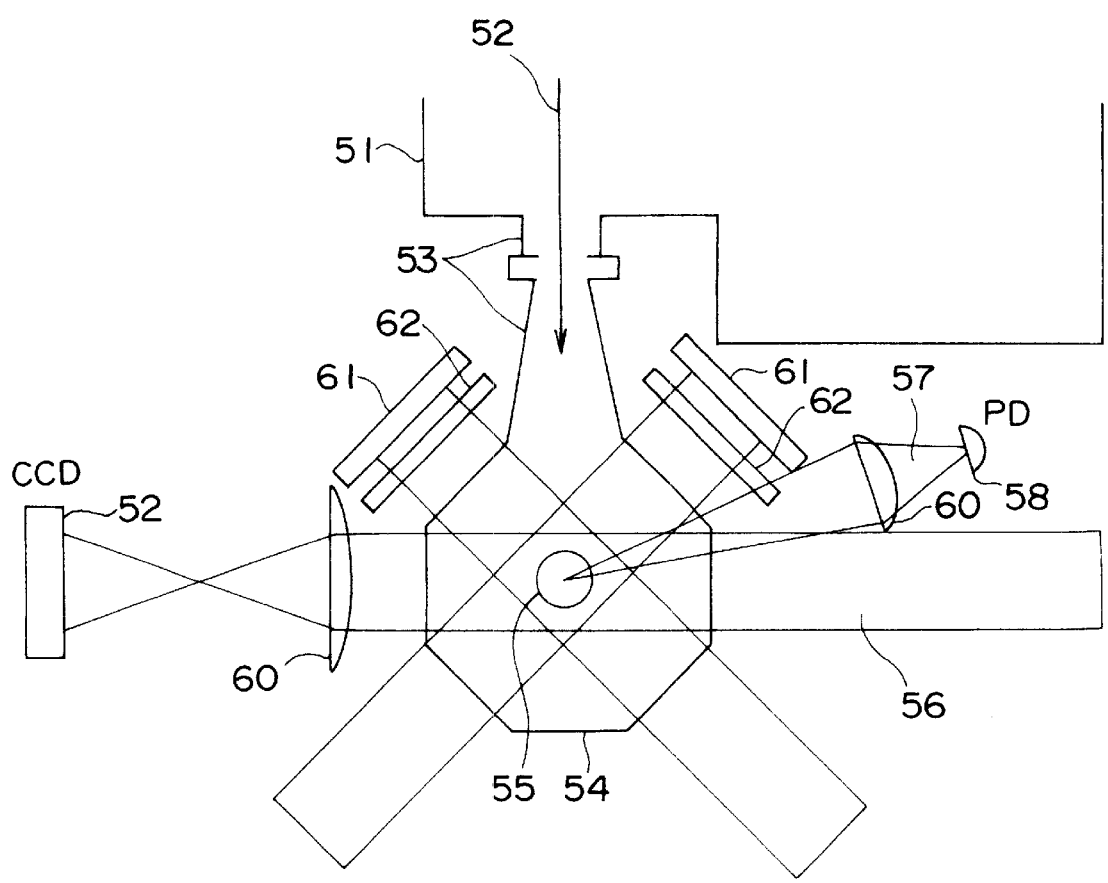
FIG. 6 is a diagrammatic view for the illustration of a process of measuring the flow rate of an atomic beam produced in an atomic beam generating method shown in FIG. 5.

First, mention is made of the flow measuring process used here with reference to FIG. 6. Shown in FIG. 6 is a diagrammatic view for the illustration of a process of measuring the flow rate of an atomic beam. As shown in FIG. 6, an atomic beam 52 is formed from a low temperature atomic cloud formed in an upper vacuum chamber 51 using an apparatus similar to the double magneto-optical trapping apparatus 20 shown in FIG. 2, and is transported via a transport tube 53 into a magneto-optical trap in a lower vacuum chamber 54 where a low temperature atomic cloud 55 is formed again from it.

The atoms in the low temperature atomic cloud 55 absorb a probe laser light 56 that resonates with the atoms. Since the amount of absorption is proportional to the number of the atoms in the low temperature atomic cloud 55, calibrating an amount of absorption me sured by CCD camera by the known amount of absorption by one atom gives the number of the atoms. The low temperature atomic cloud 55 also emits a fluorescent light 57. Since the intensity of the emitted light is proportional to the number of the atoms, the number of the atoms can easily be determined from a measured intensity of the fluorescent light, here measured using a photo diode 58, and the calibrated value preliminarily found in the absorption process.

Shown further is a condensing lens 60 as well as a mirror 61 and a wave plate 62 for optical trapping.

The flow rate of the atomic beam shown in FIG. 5 was derived from measuring by means of the photo diode 58 changes of the atomic number starting from the atomic beam 52 nil at, and at points of time timed from, the instant t=0 at which the atomic beam 52 was drawn after the low temperature atomic cloud 55 had disappeared.

The flow rate of the atomic beam shown in FIG. 5 was found from the number of the atoms of the low temperature atomic cloud 55 entrapped by the magneto-optical trap in the vacuum chamber 54. Not that all the atoms contained in the atomic beam 52 are trapped, but these results give the lower limit of the flow rate of the atomic beam 52.

The flow rate of an atomic beam was found to be $1.0\times10^7$ atoms per second when the position adjustment coil 32 shown in FIG. 3 had no current passed therethrough and when the low temperature atomic cloud 33 was located upwards (in the state shown in FIG. 4(A)). On the other hand, the flow rate of an atomic beam was found to be $1.5\times10^7$ atoms per second when the position adjustment coil 32 had an electric current passed therethrough and when the low temperature atomic cloud 33 was located near the center (in the state shown in FIG. 4(B)). Further, the flow rate of an atomic beam was found to be $3.3\times10^7$ atoms per second when the position adjustment coil 32 had an increased electric current passed therethrough and when the low temperature atomic cloud 33 was located downwards (in the state shown in FIG. 4(C)). It has thus been shown that the flow rate of an atomic beam becomes the greatest when the low temperature atomic cloud is forced downwards to an extent that the magneto-optical trap in the upper vacuum chamber 21 is almost broken.

Mention is next made of still another form of embodiment of the low velocity atomic beam according to the present invention.

Figure 7:
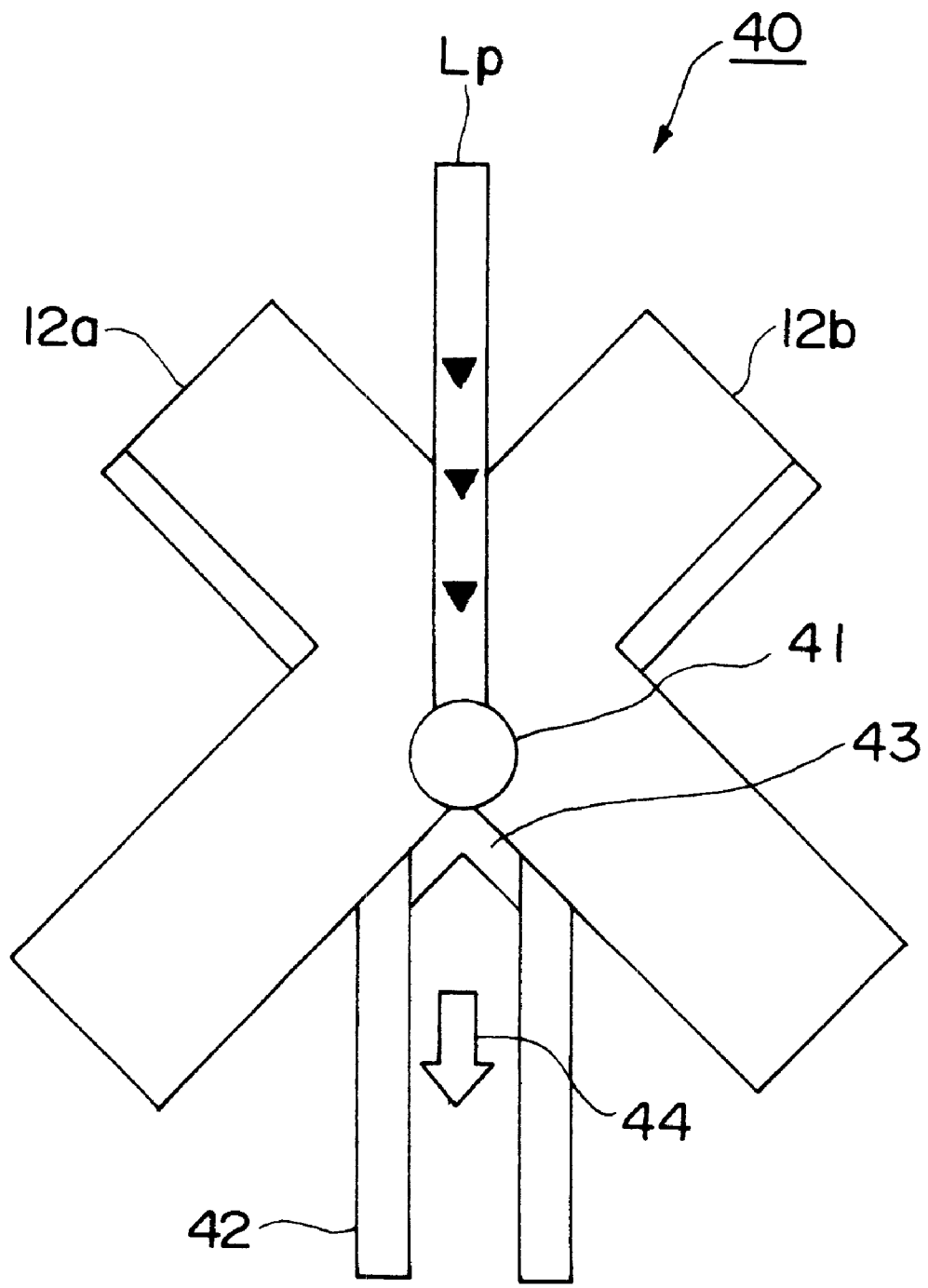
FIG. 7 is a diagrammatic view for the illustration of an atomic beam generating method according to another form of embodiment of the present invention.

FIG. 7 is a diagrammatic view for the illustration of such a low velocity atomic beam generating method. As shown in FIG. 7, an atomic beam generating apparatus 40 is constructed by incorporating in the construction of the atomic beam generating apparatus 10 shown in FIG. 1, a laser beam Lp designed to force out atoms in a low temperature atomic cloud 41.

This laser beam Lp is oriented in alignment with the central axis of a transport tube 42 to irradiate the low temperature atomic cloud 41 from the side opposite to the side in which the transport tube 42 is located. The laser beam Lp has a wavelength selected such that it resonates with atoms in the low temperature atomic cloud 41. For example, for Rb atoms, use is made of a laser beam having a wavelength of 780 nm.

If the low temperature atomic cloud 41 is irradiated with the laser beam Lp, then those of the atoms in the low temperature atomic cloud which are irradiated with the laser beam Lp are forced out into the laser beam shading zone 43, thereby generating an atomic beam 44 in the transport tube 42.

Mention is next made of a specific implementation of the low velocity atomic beam described above.

Figure 8:
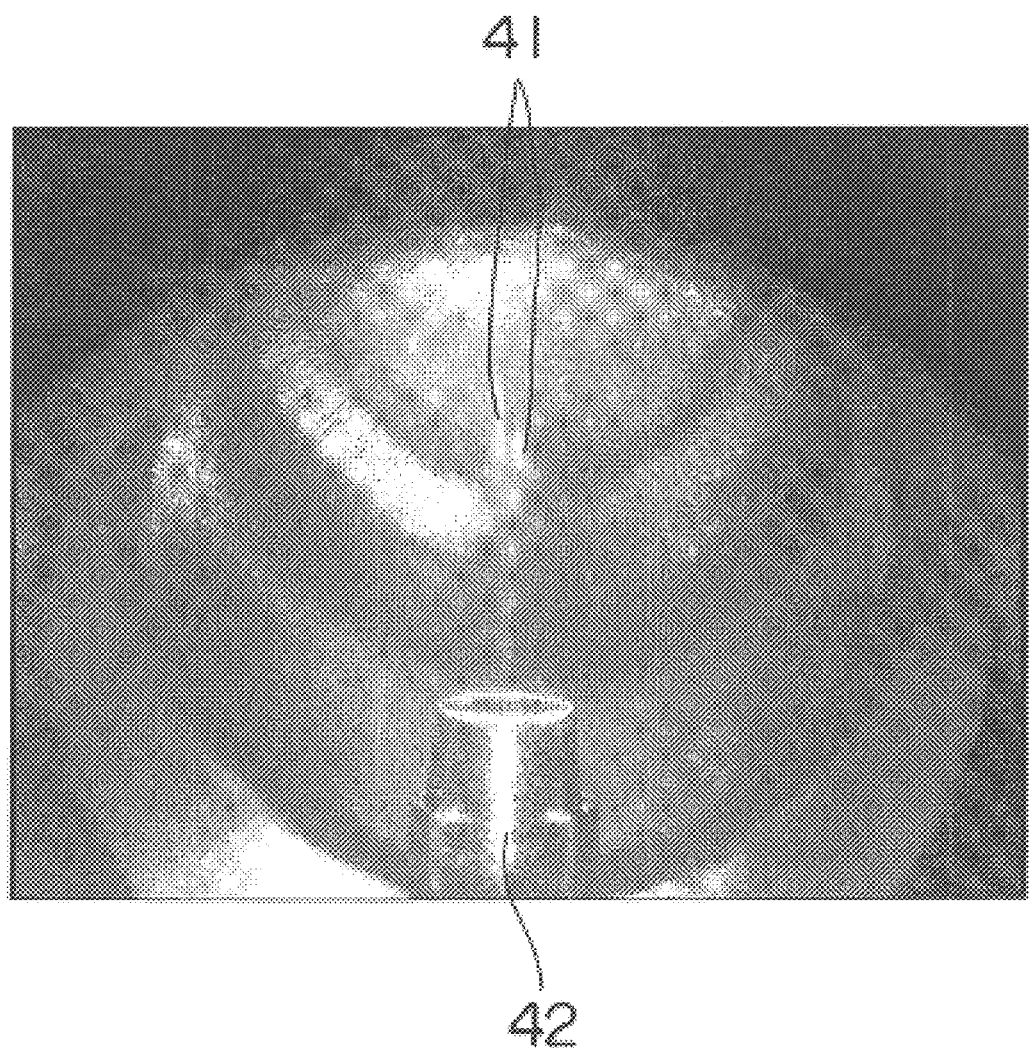
FIG. 8 shows a typical picture image, taken by the CDD camera, of an atomic beam whose flow rate is adjusted using the atomic beam generating apparatus shown in FIG. 7.

FIG. 8 shows a typical picture image, taken by the CDD camera, of an atomic beam whose flow rate is adjusted using the atomic beam generating apparatus 40 shown in FIG. 7. A laser beam Lp squeezed to be thin is applied from the above, which having a wavelength of 780 nm resonates with Rb atoms. It is seen that the low temperature atomic cloud 41 has a hole made in a region of its center, beneath which atoms are seen effusing thin in the form of a jet and forced out into a laser beam shading zone 43.

Figure 9:
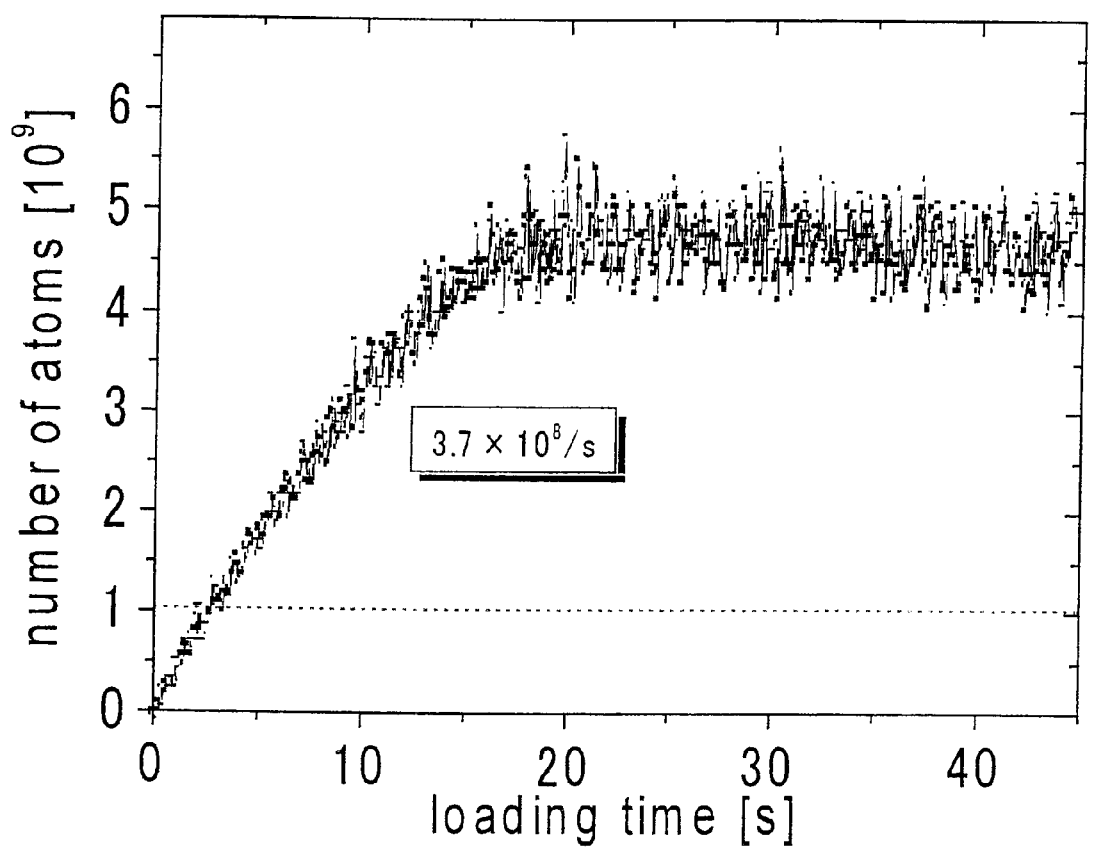
FIG. 9 shows typical results of measurement in which the flow rate of an atomic beam in the state indicated in FIG. 8 is measured.
Figure 10:
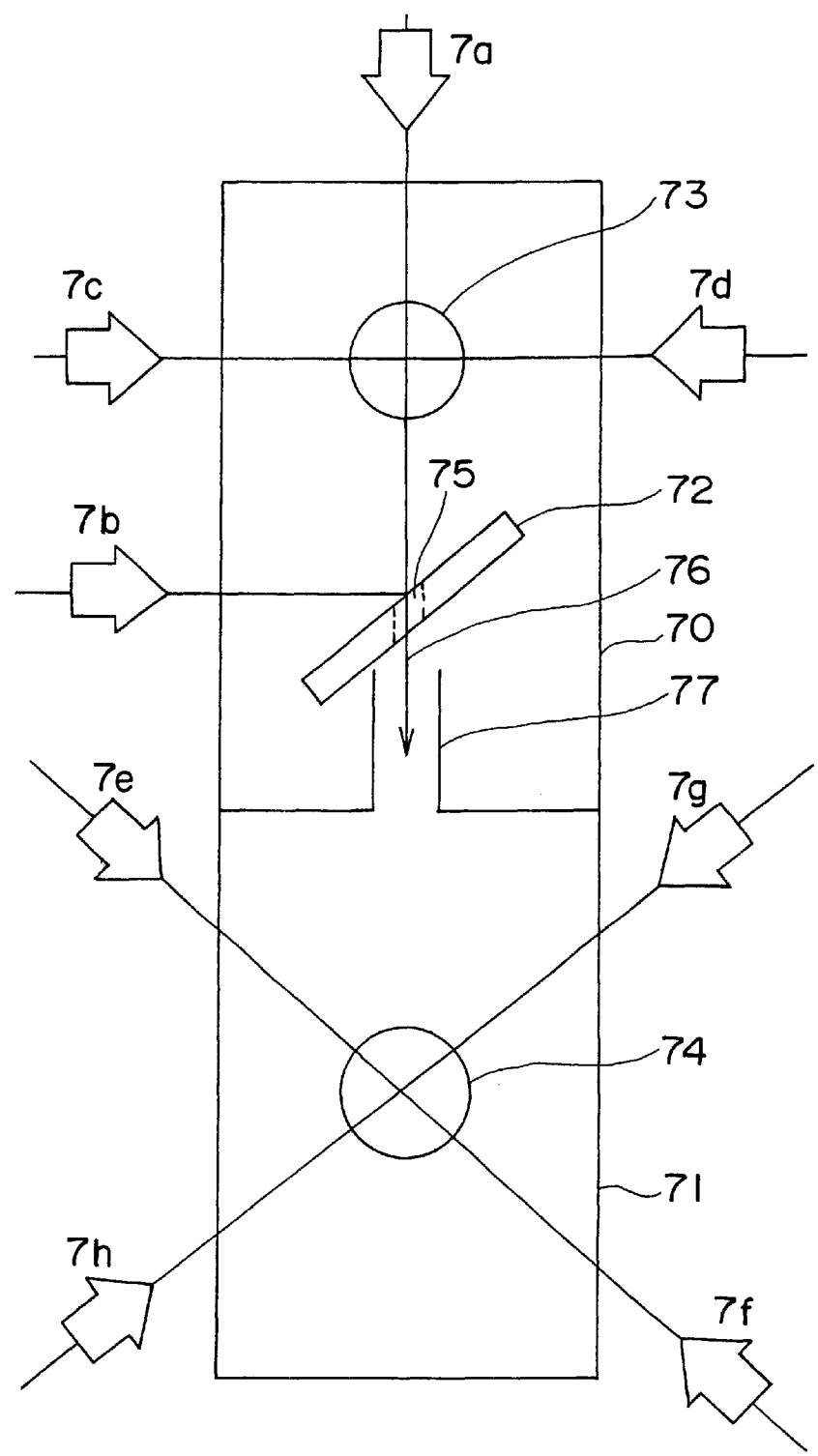
FIG. 10 is a diagrammatic view for the illustration of the conventional method in which extraction is effected using a hole formed mirror where a shade is provided for one of cooling laser beams for the purpose of extracting atoms.

FIG. 9 shows a typical set of results of measurement in which the flow rate of an atomic beam in the state indicated in FIG. 8 is measured. The flow rate was measured in the same manner as described in connection with FIG. 5. The flow rate in this case has been found to be $3.7\times10^8$ atoms per second and is seen to be still higher.

While the present invention has hereinbefore been set forth with respect to certain illustrative forms of embodiment thereof, it will readily be appreciated to be obvious to a person skilled in the art that many alternations thereof, omissions therefrom and additions thereto can be made without departing from the essences of scope of the present invention. Accordingly, it should be understood that the invention is not intended to be limited to the specific forms of embodiment thereof set forth below, but to include all possible forms of embodiment thereof that can be made within the scope with respect to the features specifically set forth in the appended claims and encompasses all the equivalents thereof.

INDUSTRIAL APPLICABILITY

As will be appreciated from the foregoing description, the present invention provides an atomic beam generating method and apparatus in which atoms are irradiated with at least two sets of laser lights in a region of laser beam intersection in which they intersect, each of the sets of laser lights being made of a pair of laser beams which are opposite in direction of travel to each other, the laser beams intersecting in the region of laser beam intersection. And in this region of laser beam intersection, a laser beam shading zone is provided in which one of the laser beams in each of the sets of laser lights that is traveling in a particular direction is obstructed to provide a shade therefor, the laser beam shading zone being so located in the region of laser beam intersection that in the laser beam shading zone a force is brought about that is effective to force atoms in the laser beam shading zone to move towards a preselected direction, thereby forming a beam thereof. The laser beam shading zone is specifically created by a tube that transports the formed beam of atoms. Accordingly, an atomic beam is generated thereby efficiently.

Also, in this atomic beam generating method and apparatus, there is no longer a mirror incorporated in vacuum equipment, and this feature makes the vacuum equipment simpler in construction and the mirror free from contamination. Hence, the extraction of an atomic beam is effected efficiently.

Another feature of an atomic beam generating method and apparatus is the disuse of the system that makes it necessary to change the internal state of atoms in order to extract the atoms. This feature makes the method and apparatus applicable to atoms of practically all of the atomic species.

A further advantage of an atomic beam generating method and apparatus according to the present invention, namely the ability to variably adjust the flow rate of an atomic beam to be produced, is gained by varying the distance between the magneto-optically entrapped low temperature atomic cloud and the transport tube adjustably using either magnetic or optical means.

Accordingly, it will be seen that such an atomic beam generating method and apparatus of the present invention is usable as an effective source of an atomic beam in various technical fields such as high resolution spectroscopy, frequency standard, atomic wave interferometers, Bose condensation atom formation, atomic ray lithography and atomic ray surface analysis.

What is claimed is:

1. An atomic beam generating method for producing an atomic beam by extracting atoms from a low temperature atomic cloud formed utilizing laser cooling, the method comprising the steps of:

forming a low temperature atomic cloud by irradiating the atoms with at least two sets of laser lights in a region of laser beam intersection in which they intersect, each of the sets of laser lights being made of a pair of laser beams which are opposite in direction of travel to each other, the laser beams intersecting in said region of laser beam intersection; and providing in said region of laser beam intersection a laser beam shading zone in which a portion of one of the laser beams in each of the sets of laser lights that is traveling in a particular direction is obstructed to provide a shade therefor, wherein said laser beam shading zone is so located in said region of laser beam intersection that in said laser beam shading zone a force is brought about that is effective to force atoms in said laser beam shading zone to move towards a preselected direction, thereby forming a beam thereof.

2. An atomic beam generating method as set forth in claim 1 wherein said laser beam shading zone is created by a tube for transporting said beam of atoms, said tube obstructing said portion of one of the laser beams in each of the sets to provide said shade therefor.

3. A laser beam generating method as set forth in claim 2, further comprising the step of adjusting the flow rate of said beam of atoms that said atomic beam transporting tube transports, by applying a magnetic field to said low temperature atomic cloud to change its position so as to change the distance between said low temperature atomic cloud and an upper end of said atomic beam transporting tube.

4. A laser beam generating method as set forth in claim 2, further comprising the step of adjusting the flow rate of said beam of atoms by irradiating said low temperature atomic cloud with an additional laser beam to force atoms in said low temperature atomic cloud aside into said laser beam shading zone.

5. An atomic beam generating method as set forth in claim 4 wherein said additional laser beam has a wavelength with which it resonates with atoms in said low temperature atomic cloud.

6. An atomic beam generating apparatus for producing an atomic beam by extracting atoms from a low temperature atomic cloud formed utilizing laser cooling, the apparatus comprising:

a laser system with at least two sets of laser lights in a region of laser beam intersection in which they intersect, each of the sets of laser lights being made of a pair of laser beams which are opposite in direction of travel to each other; and a means for providing in said region of laser beam intersection a laser beam shading zone in which a portion of one of the laser beams in each of the sets of laser lights that is traveling in a particular direction is obstructed to provide a shade therefor, wherein said means so locates the said laser beam shading zone in said region of laser beam intersection that in said laser beam shading zone a force is brought about that is effective to force atoms in said laser beam shading zone to move towards a preselected direction, thereby forming a beam thereof.

7. An atomic beam generating apparatus as set forth in claim 6 wherein said means for providing the laser beam shading zone comprises a tube for transporting said beam of atoms, said tube being arranged to obstruct said one of the laser beams in each of the sets, thereby providing said shade therefor.

8. A laser beam generating apparatus as set forth in claim 7, further comprising a means for applying a magnetic field to said low temperature atomic cloud to change its position in said region of laser beam intersection so as to change the distance between said low temperature atomic cloud and an upper end of said atomic beam transporting tube, thereby adjusting the flow rate of said beam of atoms that said atomic beam transporting tube transports.

9. A laser beam generating apparatus as set forth in claim 7, wherein said laser system is adapted to irradiate said low temperature atomic cloud with an additional laser beam to force atoms in said low temperature atomic cloud aside into said laser beam shading zone, thereby adjusting the flow rate of said beam of atoms.

10. An atomic beam generating apparatus as set forth in claim 9 wherein said additional laser beam has a wavelength with which it resonates with atoms in said low temperature atomic cloud.

* * * * *